(12) United States Patent
Stuckert et al.

(10) Patent No.: US 9,296,671 B2
(45) Date of Patent: *Mar. 29, 2016

(54) METHOD AND SYSTEM FOR PRODUCING METHANOL USING AN INTEGRATED OXYGEN TRANSPORT MEMBRANE BASED REFORMING SYSTEM

(71) Applicants: Ines C. Stuckert, East Amherst, NY (US); Shrikar Chakravarti, East Amherst, NY (US); Raymond Francis Drnevich, Clarence Center, NY (US)

(72) Inventors: Ines C. Stuckert, East Amherst, NY (US); Shrikar Chakravarti, East Amherst, NY (US); Raymond Francis Drnevich, Clarence Center, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 93 days.

This patent is subject to a terminal disclaimer.

(21) Appl. No.: 14/078,859

(22) Filed: Nov. 13, 2013

(65) Prior Publication Data

US 2014/0323597 A1 Oct. 30, 2014

Related U.S. Application Data

(60) Provisional application No. 61/874,077, filed on Sep. 5, 2013, provisional application No. 61/816,326, filed on Apr. 26, 2013, provisional application No. 61/816,330, filed on Apr. 26, 2013.

(51) Int. Cl.
*C07C 29/151* (2006.01)
*C01B 3/38* (2006.01)
*C01B 13/02* (2006.01)

(52) U.S. Cl.
CPC ............ *C07C 29/1518* (2013.01); *C01B 3/384* (2013.01); *C01B 13/0251* (2013.01);
(Continued)

(58) Field of Classification Search
CPC C07C 29/1518; C07C 31/04; C01B 13/0251; C01B 2203/0233; C01B 2203/0244; C01B 2203/0283; C01B 2203/0405; C01B 2203/043; C01B 2203/061; C01B 2203/0805; C01B 2203/0894; C01B 2203/1258; C01B 2203/142; C01B 2203/148; C01B 3/00; C01B 3/384
USPC .......................................... 518/703; 422/187
See application file for complete search history.

(56) References Cited

U.S. PATENT DOCUMENTS 4,650,814 A 3/1987 Keller
5,975,130 A 11/1999 Ligh et al.
(Continued)

FOREIGN PATENT DOCUMENTS

EP 0 926 096 A1 6/1999
EP 0 984 500 A2 3/2000
(Continued)

OTHER PUBLICATIONS

Friedemann Marschner et al., "Gas Production", Ullmann's Encyclopedia of Industrial Chemistry, Jun. 15, 2000, pp. 1-21, XP002253967.

(Continued)

*Primary Examiner* — Jafar Parsa
*Assistant Examiner* — Amy C Bonaparte
(74) *Attorney, Agent, or Firm* — Ralph J. Mancini

(57) ABSTRACT

A method and system for producing methanol that employs an integrated oxygen transport membrane based reforming system is disclosed. The integrated oxygen transport membrane based reforming system carries out a primary reforming process, a secondary reforming process, and synthesis gas conditioning to produce synthesis gas having a desired module of between about 2.0 and 2.2 for a methanol production process thereby optimizing the efficiency and productivity of the methanol plant.

21 Claims, 5 Drawing Sheets

(52) U.S. Cl.
CPC . *C01B2203/0233* (2013.01); *C01B 2203/0244* (2013.01); *C01B 2203/0283* (2013.01); *C01B 2203/043* (2013.01); *C01B 2203/0405* (2013.01); *C01B 2203/061* (2013.01); *C01B 2203/0805* (2013.01); *C01B 2203/0894* (2013.01); *C01B 2203/1258* (2013.01); *C01B 2203/142* (2013.01); *C01B 2203/148* (2013.01)

(56) References Cited

U.S. PATENT DOCUMENTS

| | | | |
|---|---|---|---|
| 6,048,472 | A | 4/2000 | Nataraj et al. |
| 6,110,979 | A * | 8/2000 | Nataraj et al. ............... 518/704 |
| 6,114,400 | A | 9/2000 | Nataraj et al. |
| 6,214,314 | B1 | 4/2001 | Abbott |
| 6,293,084 | B1 | 9/2001 | Drnevich et al. |
| 6,296,686 | B1 | 10/2001 | Prasad et al. |
| 6,382,958 | B1 | 5/2002 | Bool, III et al. |
| 6,394,043 | B1 | 5/2002 | Bool, III et al. |
| 6,562,104 | B2 | 5/2003 | Bool, III et al. |
| 7,261,751 | B2 | 8/2007 | Dutta et al. |
| 7,470,811 | B2 | 12/2008 | Thiebaut |
| 7,786,180 | B2 | 8/2010 | Fitzpatrick |
| 7,856,829 | B2 | 12/2010 | Shah et al. |
| 8,196,387 | B2 | 6/2012 | Shah et al. |
| 8,262,755 | B2 | 9/2012 | Repasky et al. |
| 8,349,214 | B1 | 1/2013 | Kelly et al. |
| 8,419,827 | B2 | 4/2013 | Repasky et al. |
| 2003/0039608 | A1 | 2/2003 | Shah et al. |
| 2004/0221722 | A1 | 11/2004 | Prasad et al. |
| 2007/0041894 | A1 | 2/2007 | Drnevich |
| 2007/0289215 | A1 | 12/2007 | Hemmings et al. |
| 2007/0292342 | A1 | 12/2007 | Hemmings et al. |
| 2008/0141672 | A1 | 6/2008 | Shah et al. |
| 2008/0302013 | A1 | 12/2008 | Repasky et al. |
| 2009/0120379 | A1 | 5/2009 | Bozzuto et al. |
| 2011/0076213 | A1 | 3/2011 | Carolan et al. |
| 2011/0142722 | A1 | 6/2011 | Hemmings et al. |
| 2011/0180399 | A1 * | 7/2011 | Christie et al. ............... 204/295 |
| 2013/0009100 | A1 * | 1/2013 | Kelly et al. ............... 252/373 |
| 2013/0009102 | A1 | 1/2013 | Kelly et al. |
| 2014/0183866 | A1 | 7/2014 | Kromer et al. |
| 2014/0319424 | A1 | 10/2014 | Chakravarti et al. |
| 2014/0319427 | A1 | 10/2014 | Chakravarti et al. |
| 2014/0323598 | A1 * | 10/2014 | Chakravarti et al. .......... 518/703 |
| 2014/0323599 | A1 * | 10/2014 | Chakravarti et al. .......... 518/704 |

FOREIGN PATENT DOCUMENTS

| | | |
|---|---|---|
| EP | 0 989 093 A2 | 3/2000 |
| EP | 1 504 811 A1 | 2/2005 |
| WO | WO 2013/062413 A1 | 5/2013 |
| WO | WO 2014/107707 A2 | 7/2014 |
| WO | WO 2014/176022 A1 | 10/2014 |

OTHER PUBLICATIONS

Lee Rosen, Nick Degenstein; Minish Shah; Jamie Wilson; Sean Kelly; John Peck; and Max Christie; "Development of Oxygen Transport Membranes for Coal-Based Power Generation"; ScienceDirect (Available online at www.sciencedirect.com); Energy Procedia 4 (2011) pp. 750-755.

* cited by examiner

US 9,296,671 B2

METHOD AND SYSTEM FOR PRODUCING METHANOL USING AN INTEGRATED OXYGEN TRANSPORT MEMBRANE BASED REFORMING SYSTEM

CROSS REFERENCE TO RELATED APPLICATIONS

This application claims priority to and the benefit of U.S. provisional patent application Ser. Nos. 61/874,077 filed on Sep. 5, 2013; 61/816,326 filed on Apr. 26, 2013; and 61/816,330 filed on Apr. 26, 2013, the disclosures of which are incorporated by reference herein.

FIELD OF THE INVENTION

The present invention relates to a method and system for producing methanol using an oxygen transport membrane based reforming system as a source of synthesis gas, and more particularly, a method and system for producing a synthesis gas for a methanol production facility using an oxygen transport membrane based reforming system that provides both primary and secondary reforming.

BACKGROUND

The methanol production process generally involves directing a compressed synthesis gas comprising hydrogen, carbon monoxide and carbon dioxide at an elevated temperature and pressure to a methanol converter reactor containing one or more beds of a methanol synthesis catalyst such as a copper and zinc oxide catalyst. The carbon monoxide and carbon dioxide in the synthesis gas react with the hydrogen to form methanol across the catalyst. The methanol synthesis process is usually operated in a loop where a portion of the compressed synthesis gas is converted to methanol each pass through the methanol converter reactor. Methanol product is recovered by cooling the methanol product gas stream to a temperature below the dew point of the methanol such that crude methanol and water condense out, with the remaining gas being recycled through the methanol converter reactor. The crude methanol and water produced in the methanol converter reactor are typically reduced in pressure in a let-down or "flash" vessel. Since most crude methanol contains a large range of impurities, the crude methanol must be purified so as to remove such impurities to produce methanol of chemical grade quality. The preferred technique used for methanol purification is a distillation process.

Synthesis gas is typically characterized by the stoichiometric ratio (H2−CO2)/(CO+CO2), often referred to as the module. A module of about 2.0 defines the desired stoichiometric ratio of synthesis gas for the production of methanol. Other important properties of the synthesis gas in methanol production include the carbon monoxide to carbon dioxide ratio and the concentration of inerts in the synthesis gas. A high carbon monoxide to carbon dioxide ratio typically increases the reaction rate and the achievable per pass conversion while concurrently decreases the formation of water thereby reducing the catalyst deactivation rate. A high concentration of inerts in the synthesis gas, such as methane, argon, nitrogen, etc. typically lowers the partial pressure of the active reactants. Since the methanol conversion reaction is exothermic, lower temperatures favor conversion of the synthesis gas to methanol. Pressure will also affect the methanol conversion reaction, with increasing pressure also favoring methanol formation.

In many methanol production facilities, the incoming compressed synthesis gas is often mixed with recycled unreacted gas stream to form the synthesis gas stream that is supplied to the methanol converter reactor. A portion of the unreacted gas stream may be purged to prevent the buildup of inerts in the methanol converter reactor. The amount of purge flow typically varies anywhere from 1% to 6% of the total unreacted gas stream and often depends on the amount of inerts in the incoming synthesis gas, with higher level of inerts generally requiring higher purge flows and lower level of inerts generally requiring lower purge flows.

The challenge facing many methanol producers is to optimize the integration of the synthesis gas production or front-end of the methanol plant with the methanol synthesis or back-end of the methanol plant. Integration of the front-end synthesis gas production with the methanol synthesis or back-end of the methanol plant has to date focused on use of the purge flow from the methanol synthesis section in the synthesis gas production section and use of heat recovery systems that efficiently utilize excess heat generated in both sections of the methanol plant.

The purge flow containing unconverted hydrogen and/or methane slip can also be recovered and recycled back to the front-end or synthesis gas producing portion of the methanol plant. Similarly, the excess heat generated in the exothermic methanol conversion reaction is typically used to pre-heat synthesis gas feed to methanol synthesis section, to generate saturated steam, to pre-heat the reformer feed streams and/or to heat boiler feed water used in the synthesis gas production process. Some of the prior art uses of the purge stream include use of the hydrogen and/or methane slip in the purge stream as a feed or source of fuel to be used in the front-end steam methane reforming (SMR), partial oxidation (POx), autothermal reforming (ATR) processes. Other prior art has suggested the recovery of hydrogen from the purge stream and mixing the recovered hydrogen with the synthesis gas to improve the module of synthesis gas for methanol production.

As used herein, steam methane reforming (SMR) is a catalytic conversion of natural gas, including methane and light hydrocarbons, to synthesis gas containing hydrogen and carbon monoxide by reaction with steam. The reactions are endothermic, requiring significant amount of energy input. The steam methane reforming process is carried out at high temperatures with the catalyst inside tubes within a fired furnace. The amount of steam used is in excess of the reaction stoichiometry requirements, as required to prevent the catalyst from coking. No oxygen is used in steam methane reforming.

Partial oxidation, on the other hand, is a non-catalytic process where a sub-stoichiometric amount of oxygen is allowed to react with the natural gas creating steam and carbon dioxide at high temperatures. The residual methane is reformed through reactions with the high temperature steam and carbon dioxide to produce synthesis gas. Autothermal reforming is a variant of the partial oxidation process, but which uses a catalyst to permit reforming to occur at lower temperatures than the POx process.

Many synthesis gas generation methods also employ pre-reforming and secondary reforming. When the feedstock contains significant amounts of heavy hydrocarbons, SMR and ATR processes are typically preceded by a pre-reforming step. As generally known in the art, pre-reforming is a catalyst based process for converting higher hydrocarbons to methane, hydrogen, carbon monoxide and carbon dioxide. The reactions involved in pre-reforming are endothermic. Most pre-reformers operate adiabatically, and thus the pre-reformed feedstock leaves at a much lower temperature than the feedstock entering the pre-reformer. A secondary reforming process conventionally refers to an autothermal reforming process that is fed product from a SMR process. Thus, the feed to a secondary reforming process is primarily synthesis gas from the SMR. Depending on the end application, some natural gas may bypass the SMR process and be directly introduced into the secondary reforming process. Also, when a SMR process is followed by a secondary reforming process, the SMR may operate at a lower temperature, e.g. 650° C. to 800° C. versus 850° C. to 950° C.

A synthesis gas with a module less than about 2.0 signifies that the synthesis gas is deficient in hydrogen for the production of methanol. In such a case, the hydrogen will be consumed in the methanol synthesis reaction while a substantial portion of the carbon monoxide and carbon dioxide remain unreacted leading to a recycle stream of unreacted gas which has high levels of carbon monoxide and carbon dioxide but is low in hydrogen. This causes several disadvantages including higher volume of catalysts and increased production of unwanted by-products, namely higher alcohols and ketones. The module of crude synthesis gas is often determined by the reforming process used. Reforming processes such as partial oxidation (POx) and autothermal reforming (ATR) generally producing hydrogen deficient synthesis gas.

To remedy the hydrogen deficiency of synthesis gas, it has been suggested to recover hydrogen from the purge stream using a hydrogen recovery unit such as a hydrogen pressure swing adsorption (PSA) unit or hydrogen separation membrane. The recovered hydrogen is recycled back into the synthesis gas so that the gas within the methanol synthesis loop is significantly more hydrogen rich than the originally produced synthesis gas. An alternative method to remedy the hydrogen deficiency of synthesis gas is to take a side-stream of the original produced synthesis gas and recover hydrogen from it using a hydrogen pressure swing adsorption (PSA) unit or hydrogen separation membrane and feeding the recovered hydrogen back into the synthesis gas directed to the methanol synthesis reactor. See U.S. Pat. Nos. 7,786,180; 7,470,811; and 4,650,814. U.S. Pat. No. 7,786,180 likely represents the closest prior art in the field of methanol synthesis where hydrogen is recovered using a hydrogen recovery unit from both the purge gas and a portion of the original synthesis gas or make up gas. The recovered hydrogen is simply added to the synthesis gas mixture that is directed to the methanol synthesis reactor.

However, the above-identified solutions are limited to addressing the hydrogen deficiency of synthesis gas and are customized or tailored for use with conventional reforming processes such as steam methane reforming (SMR), partial oxidation (POx), autothermal reforming (ATR) or combinations thereof.

As can be appreciated, these conventional methods of producing a synthesis gas are expensive and involve complex installations. In order to overcome the complexity and expense of such installations it has been proposed to generate the synthesis gas within reactors that utilize an oxygen transport membrane to supply oxygen and thereby generate the heat necessary to support endothermic heating requirements of the steam methane reforming reactions. See, for example, U.S. Pat. Nos. 6,048,472; 6,110,979; 6,114,400 and 6,296,686. However, none of these oxygen transport membrane based reforming arrangements adequately integrate the downstream process with the front-end reforming process in a manner that improves the productivity and cost effectiveness of a methanol production facility.

What is needed, therefore, are advances in methanol plant operations, and more particularly advances in the integration of the synthesis gas production with the methanol synthesis or back-end of the methanol plant where some or all of the synthesis gas is produced using an oxygen transport membrane systems.

SUMMARY OF THE INVENTION

The present invention may be characterized as a method for producing methanol using an oxygen transport membrane based reforming system, which consists of two reactors that can be in the form of sets of catalyst containing tubes—reforming reactor and oxygen transport membrane reactor. The method comprising the steps of: (i) separating oxygen from an oxygen containing stream with a one or more catalyst containing oxygen transport membrane reactor within the oxygen transport membrane based reforming system to produce an oxygen permeate and an oxygen depleted retentate stream, the catalyst being contained within the tubes on the permeate side of the oxygen transport membrane reactor; (ii) partially reforming a combined feed stream comprising natural gas and steam in the reforming reactor in the presence of a reforming catalyst and radiant heat transferred from the oxygen transport membrane reactor within the oxygen transport membrane based reforming system to produce a partially reformed synthesis gas stream; (iii) directing the partially reformed synthesis gas stream to the permeate side of the one or more catalyst containing oxygen transport membrane reactor; (iv) reacting a portion of the partially reformed synthesis gas stream contacting the permeate side of the catalyst containing oxygen transport membrane reactor with the oxygen permeate to generate a reaction product stream and heat, and wherein a portion of the heat is the radiant heat used in the partial reforming step in the reforming reactor, a portion of the heat is used within the oxygen transport membrane reactor, and a portion of the heat is transferred by convection to the oxygen-depleted retentate stream; (v) reforming the partially reformed synthesis gas stream in the catalyst containing oxygen transport membrane tubes in the presence of a portion of the heat generated as a result of the reaction to produce a final reformed synthesis gas product stream; and (vi) directing the final reformed synthesis gas product stream to a methanol synthesis and purification system where it is converted to a finished methanol product.

A key aspect of the present invention is the capability or feature that allows adjustment of the synthesis gas module to the desired range of 2.0 to 2.2 for methanol conversion. To achieve this module, one may divert a portion of the cooled synthesis gas stream to a module management system to produce hydrogen gas via a water gas shift reaction and hydrogen separation and re-combine a portion of the produced hydrogen with the remaining portion of the synthesis gas stream to produce a combined synthesis gas product stream having a module between about 2.0 to 2.2. Alternatively, adjustment of the synthesis gas module may be accomplished by recycling a portion of the unconverted hydrogen and methane slip recovered during the methanol synthesis to a hydrogen pressure swing adsorption system to produce hydrogen and re-combine a portion of the produced hydrogen with the remaining portion of the synthesis gas stream to produce a combined synthesis gas product stream having a module between about 2.0 to 2.2.

Using either module adjustment approach, it may be advantageous to direct a portion of the hydrogen generated by the module management system to the hydrocarbon feed stream prior to desulfurization. It may also be advantageous to direct a portion of any off-gas generated by the module management system to a duct burner used in the oxygen transport membrane based reforming system as a portion of the fuel stream to the duct burner.

The invention may also be characterized as a method of adjusting module of synthesis gas in methanol plant comprising the steps of: (i) reforming a combined feed stream of natural gas and steam partially in a reforming reactor in the presence of reforming catalyst and radiant heat transferred from the oxygen transport membrane reactor and then fully in the presence of an oxygen containing permeate, one or more catalysts and heat in an oxygen transport membrane reactor within the oxygen transport membrane based reforming system to produce a synthesis gas stream and an oxygen depleted retentate stream; (ii) diverting a portion of the synthesis gas stream to a module management system to generate hydrogen gas via a water gas shift reaction and hydrogen separation; (iii) combining a portion of the generated hydrogen with the remaining portion of the synthesis gas stream to produce a combined synthesis gas product stream having a module between about 2.0 to 2.2; (iv) directing the combined synthesis gas product stream to a methanol synthesis system; (v) recovering unconverted hydrogen and methane slip from the methanol synthesis system; and (vi) recycling a portion of the unconverted hydrogen and methane slip recovered during the methanol synthesis to the module management system.

The invention may also be characterized as a method of adjusting the module of a synthesis gas stream for use in a methanol plant comprising the steps of: (i) reforming a combined feed stream of natural gas and steam partially in a reforming reactor in the presence of reforming catalyst and radiant heat transferred from the oxygen transport membrane reactor and then fully in the presence of an oxygen containing permeate, one or more catalysts and heat in an oxygen transport membrane reactor within the oxygen transport membrane based reforming system to produce a synthesis gas stream and an oxygen depleted retentate stream; (ii) directing the synthesis gas stream to a methanol synthesis and purification system; (iii) recovering unconverted hydrogen and methane slip from the methanol synthesis and methanol purification system; (iv) recycling a portion of the unconverted hydrogen and methane slip recovered during the methanol synthesis and methanol purification to a hydrogen pressure swing adsorption system to generate hydrogen; and (v) combining a portion of the generated hydrogen with the synthesis gas stream to produce a combined synthesis gas product stream having a module between about 2.0 to 2.2.

Finally, the invention may also be characterized as a system for producing methanol using an oxygen transport membrane based reforming system comprising: (a) an oxygen transport membrane based reforming system configured to reform a combined feed stream of natural gas and steam to produce a synthesis gas stream; (b) a module management system configured to produce a source of supplemental hydrogen from a portion of the produced synthesis gas stream or a portion of the methanol purge stream or both, with the supplemental hydrogen stream configured to be combined with the produced synthesis gas stream to yield a modified synthesis gas product stream having a module between about 2.0 to 2.2; (c) a methanol synthesis reactor configured to receive the modified synthesis gas product stream and produce crude methanol and the methanol purge stream; and (d) a methanol purification system configured to purify the crude methanol.

BRIEF DESCRIPTION OF THE DRAWINGS

While the specification concludes with claims distinctly pointing out the subject matter that applicants regard as their invention, it is believed that the invention will be better understood when taken in connection with the accompanying drawings in which:

DETAILED DESCRIPTION

Figure 1:
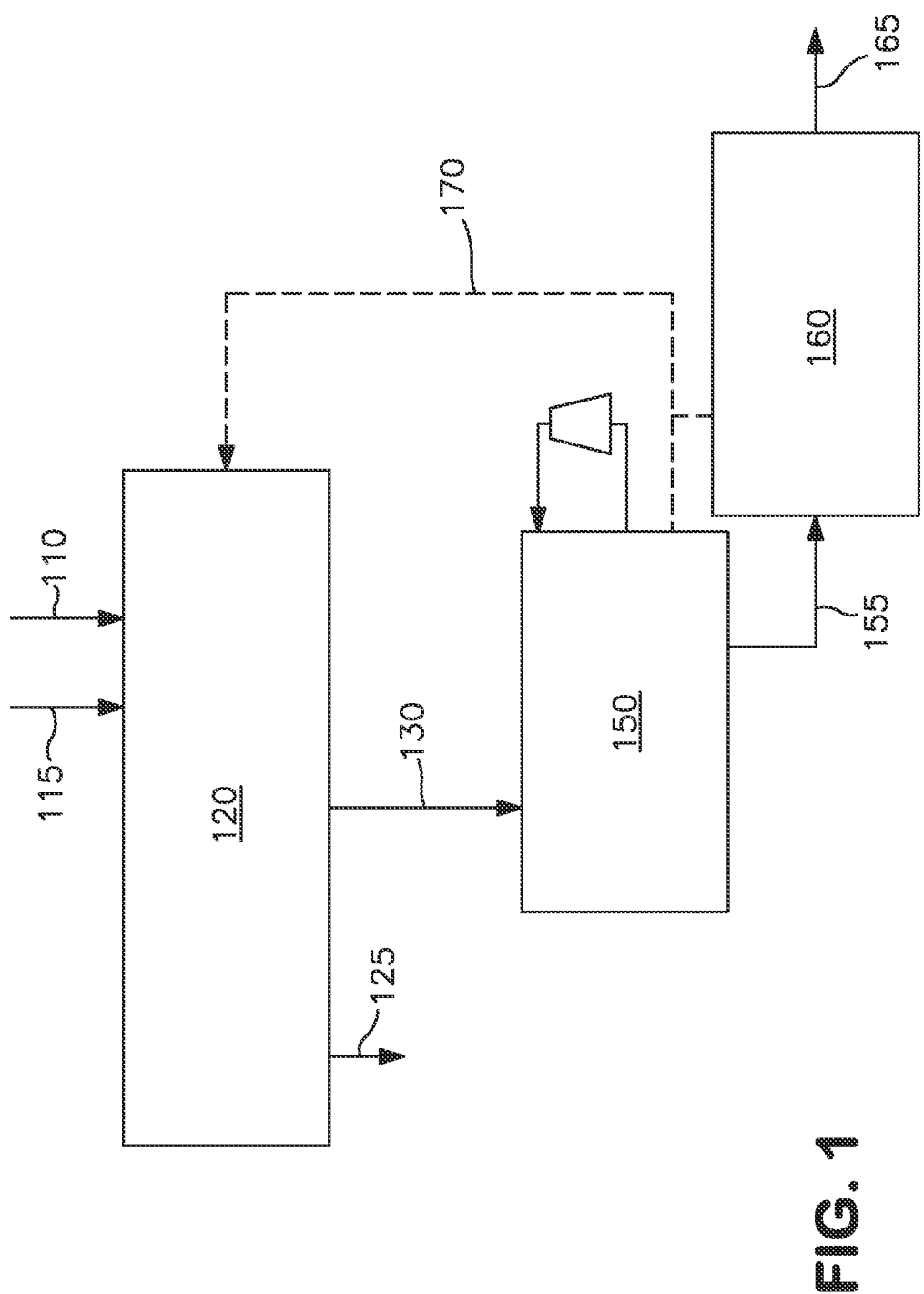
FIG. 1 is a schematic illustration of a methanol production process employing an oxygen transport membrane based reforming system in accordance with the present invention.
Figure 2:
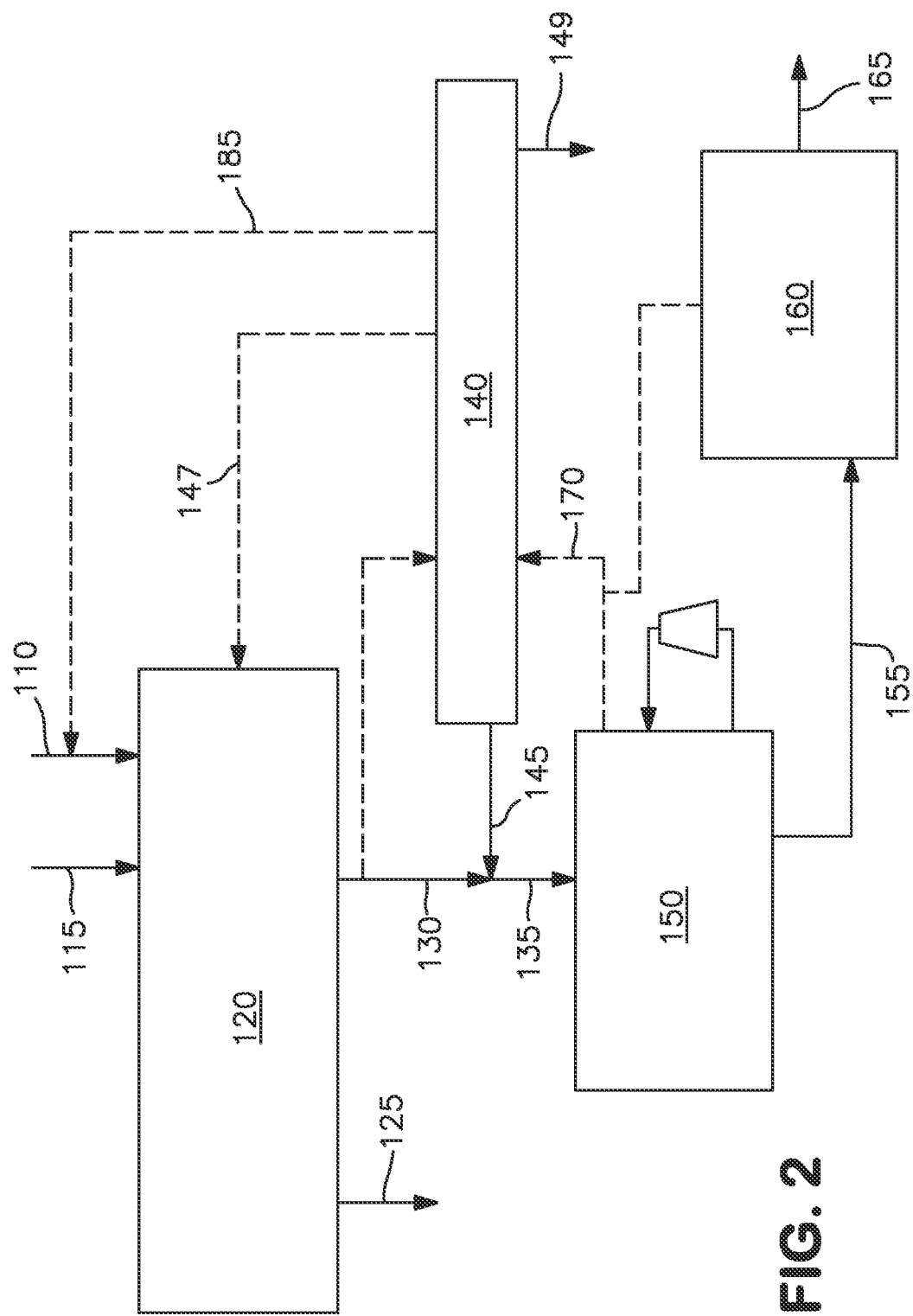
FIG. 2 is a schematic illustration of a methanol production process employing an alternate configuration of an oxygen transport membrane based reforming system.

Turning now to the drawings and particularly FIG. 1 and FIG. 2, there is shown a high level schematic illustration of an oxygen transport membrane based reforming system configured for use in methanol production operations, preferably in the design and construction of new or expanded methanol production facilities.

In FIG. 1, there is shown a partial schematic illustration of a methanol production plant employing an oxygen transport membrane based reforming system as the sole source of synthesis gas supplied to the methanol synthesis and purification system. The hydrocarbon containing feed stream 110 and air 115 are received by the oxygen transport membrane based reforming system 120 to produce a synthesis gas product 130 and a heated retentate stream 125. All or most of the resulting synthesis gas product 130 is directed to a methanol synthesis reactor 150 and where the synthesis gas product stream 130 is synthesized into crude methanol 155 and purified in a methanol purification system 160, preferably via a distillation process, into the methanol product 165. During the synthesis and purification process, a portion of the unconverted hydrogen and recoverable methane slip characterized as a methanol purge stream 170 is recirculated to the oxygen transport membrane based reforming system 120. Though not explicitly discussed, a minor portion of the purge, typically less than 10%, originates as off-gas from the purification step.

An alternate configuration of coupling an oxygen transport membrane based reforming system to a methanol production process is shown in FIG. 2. As seen therein, the hydrocarbon containing feed stream 110 and air 115 are received by the oxygen transport membrane based reforming system 120 to produce a synthesis gas product 130 and a heated retentate stream 125. A portion of the resulting synthesis gas product 130 may be directed to a module management section 140 configured to produce a supplemental hydrogen stream 145 which is recombined with the synthesis gas product 130 to form a modified synthesis gas product 135 with a module between 2.0 and 2.2. This modified synthesis gas product 135 is directed to a methanol synthesis reactor 150 where the modified synthesis gas stream 135 is synthesized into crude methanol 155 and purified in a methanol purification process 160, preferably via a distillation process, into the final methanol product 165. During the methanol synthesis process 150, a portion of the unconverted hydrogen and recoverable methane slip characterized as and contained in a methanol purge stream 170 is recirculated to module management section 140, to produce a supplemental hydrogen stream. A first portion of the supplemental hydrogen stream 185 is combined with the hydrocarbon containing feed stream 110 and a second portion of the supplemental hydrogen stream may be combined with the synthesis gas product 130 to form a modified synthesis gas product 135 with a module between 2.0 and 2.2. The module management section 140 is also configured to produce an off-gas 147 and optionally, a condensate stream 149. The off-gas 147 can be used as a fuel in the synthesis gas generation process, involving the oxygen transport membrane based reforming system, to reduce the natural gas consumption.

Figure 3:
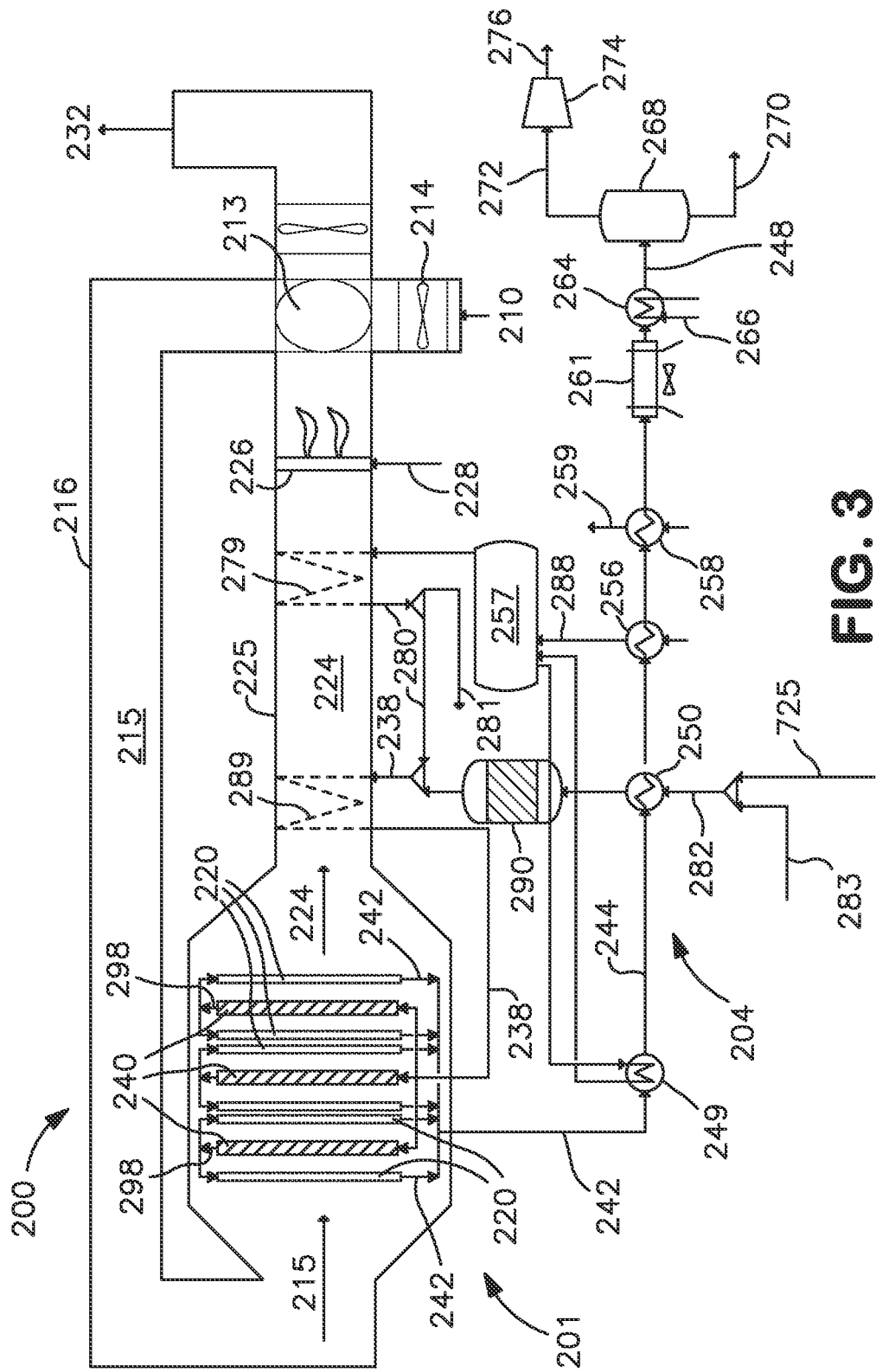
FIG. 3 is a schematic illustration of an embodiment of an oxygen transport membrane based reforming system configured to carry out a primary reforming process and a secondary reforming process for production of synthesis gas.

FIG. 3 provides a schematic illustration of an embodiment of an oxygen transport membrane based reforming system 201 and assembly 200 in accordance with the present invention. As seen therein, an oxygen containing stream 210, such as air, is introduced to the system by means of a fixed draft (FD) fan 214 into a heat exchanger 213 for purposes of preheating the oxygen containing feed stream 210. Heat exchanger 213 is preferably a high efficiency, cyclic, continuously rotating ceramic regenerator disposed in operative association with the oxygen containing feed stream 210 and the heated retentate stream 224. The ceramic regenerator 213 heats the incoming air feed stream 210 to a temperature in the range of about 850° C. to 1000° C.

The oxygen depleted air leaves the oxygen transport membrane reactor as a heated retentate stream 224 at the same or slightly higher temperature than the heated air feed stream 215. Any temperature increase, typically <30° C., is attributable to the portion of energy generated by the oxidizing reaction of hydrogen and carbon monoxide in the oxygen transport membrane tubes and transferred by convection to the air stream. The heated, oxygen depleted retentate stream 224 is first used to heat the mixed feed stream to a temperature between about 475° C. and 650° C., and more preferably to a temperature between about 525° C. and 600° C., and is subsequently used to further heat steam to superheated steam.

The temperature of this oxygen depleted retentate stream 224 preferably needs to be then increased back to a temperature between about 1000° C. and 1200° C. prior to being directed to the ceramic heat exchanger or regenerator 213. This increase in temperature of the retentate stream 224 is preferably accomplished by use of a duct burner 226, which facilitates combustion of a supplemental fuel stream 228 using some of the residual oxygen in the retentate stream 224. It is conceivable that the mixed feed heater and steam superheater could alternatively be located in a separate fired heater (not shown). In that case, the fuel requirements of the duct burner 226 will be substantially less. In the ceramic heat exchanger or regenerator 213, the heated, oxygen depleted retentate stream provides the energy to raise the temperature of the incoming feed air stream from ambient temperature to a temperature between about 850° C. and 1000° C. The resulting cold retentate stream exiting the ceramic heat exchanger, typically containing less than 5% oxygen, leaves the oxygen transport membrane based reforming system 201 system as exhaust gas 232 at a temperature of around 150° C. An alternate location for the duct burner is on air stream 215, upstream of the oxygen transport membrane reforming system 201.

As shown in FIG. 3 the oxygen transport membrane based reforming system 201 comprises two sets of tubes, including reforming tubes 240 where the primary reforming occurs and oxygen transport membrane tubes 220 where the secondary reforming occurs. Although only six secondary reforming oxygen transport membrane tubes 220 are illustrated in close proximity to three primary reforming tubes 240, as would occur to those skilled in the art, there could be many of such secondary reforming oxygen transport membrane tubes and many primary reforming tubes in each oxygen transport membrane reforming sub-system. Likewise, there would be multiple oxygen transport membrane reforming sub-systems used in an industrial application of the oxygen transport membrane based reforming system 201.

The heated oxygen containing stream 215 is directed via the intake duct 216 to a plurality of secondary reforming oxygen transport membrane tubes 220 incorporated into the oxygen transport membrane system 201. The oxygen transport membrane tubes 220 are preferably configured as multilayered ceramic tubes capable of conducting oxygen ions at an elevated operational temperature, wherein the retentate side of the oxygen transport membrane tubes 220 is the exterior surface of the ceramic tubes exposed to the heated oxygen containing stream 215 and the permeate side is the interior surface of the ceramic tubes. Within each of the oxygen transport membrane tubes 220 are one or more catalysts that facilitate secondary reforming.

The hydrocarbon containing feed stream 283, preferably natural gas, to be reformed is typically preheated to around 370° C., as described in more detail below. As natural gas typically contains unacceptably high level of sulfur species, some hydrogen gas 725 is added prior to desulfurization. The mixture 282 of the hydrogen gas 725 and hydrocarbon containing feed stream 283 is heated in heat exchanger 250 that serves as a pre-heater and then undergoes a sulfur removal process via device 290 such as hydro-treating to reduce the sulfur species to $H_2S$, which is subsequently removed in a guard bed using material like ZnO and/or CuO. The hydro-treating step also saturates any alkenes present in the hydrocarbon containing feed stream. Although not shown, the heated feed stream 282 may also undergo pre-reforming step in an adiabatic pre-reformer, which converts higher hydrocarbons to methane, hydrogen, carbon monoxide, and carbon dioxide, or in a heated pre-reformer. In the case of heated pre-reforming, it is contemplated that the catalyst based pre-reformer be thermally coupled with the oxygen transport membrane based reforming system.

Superheated steam 280 is added to the pre-treated natural gas and hydrogen feed stream, as required, to produce a mixed feed stream 238 with a steam to carbon ratio between about 1.0 and 2.5, and more preferably between about 1.2 and 2.2. The superheated steam 280 is preferably between about 300 psia and 1200 psia and between about 300° C. and 600° C. and heated by means of indirect heat exchange with the heated retentate stream 224 using steam coils 279 disposed in the retentate duct 225. Any superheated steam 280 not added or used in the natural gas and hydrogen feed 282 is exported steam 281 used for power generation. The mixed feed stream 238 is heated, by means of indirect heat exchange with the heated retentate stream using coils 289 disposed in the retentate duct 225, to preferably between about 475° C. and 650° C., and more preferably to a temperature between about 525° C. and 600° C.

The heated mixed feed stream 238 is then sent to the reforming tubes 240, which contain conventional reforming catalyst. The temperature of the partially reformed hydrogen-rich synthesis gas 298 leaving the reforming tubes 240 is typically designed to be between 650° C. and 875° C. This synthesis gas is then fed to the oxygen transport membrane tubes 220 filled with a catalyst or catalysts that would facilitate partial oxidation and reforming. Oxygen from the heated intake air permeates through the oxygen transport membrane tubes 220 and facilitates reaction of a portion of the hydrogen and carbon monoxide, and possibly some methane. A portion of the energy or heat generated by this reaction is used for in-situ reforming of the residual methane in the partially reformed synthesis gas 298. The rest of the energy or heat is transferred by radiation to the reforming tubes 240 to drive the primary reforming reactions and by convection to the oxygen-depleted air stream. The synthesis gas 242 leaving the oxygen transport membrane tubes 220, which essentially function as a secondary reformer, is at a temperature between about 900° C. and 1050° C.

The endothermic heating requirements of the reforming process occurring in the reforming tubes 240 is supplied through radiation of some of the heat from the oxygen transport membrane tubes 220 together with the convective heat transfer provided by heated retentate stream 224. In addition, as the heated, oxygen depleted retentate stream 224 exits the oxygen transport membrane based reforming system 201, it also heats the mixed feed stream 238 to a temperature between about 475° C. and 650° C. via indirect heat transfer using one or more coils 289 disposed in the retentate stream duct 225.

The synthesis gas stream 242 produced by the oxygen transport membrane based reforming system 201 generally contains hydrogen, carbon monoxide, unconverted methane, steam and carbon dioxide other constituents. A significant portion of the sensible heat from the synthesis gas stream 242 can be recovered using a heat exchange section or recovery train 204. Heat exchange section 204 is designed to cool the produced synthesis gas stream 242 exiting the oxygen transport membrane based reforming system 201. In this illustrated embodiment, the heat exchange section 204 is also designed such that in cooling the synthesis gas stream 242, process steam is generated, hydrocarbon feed stream is preheated, and boiler feed water and feedwater are heated.

To minimize metal dusting issues, the hot synthesis gas 242 is directly cooled to about 400° C. or less in a Process Gas (PG) Boiler 249. The initially cooled synthesis gas stream 244 is then used to preheat the mixture of natural gas and hydrogen feed stream 283 in a fuel pre-heater 250 and subsequently to pre-heat boiler feed water 288 in the economizer 256 and to heat the feed water stream 259. In the illustrated embodiment, the boiler feed water stream 288 is preferably pumped using a feed water pump (not shown), heated in economizer 256 and sent to steam drum 257 while the heated feed water 259 is sent to a de-aerator (not shown) that provides boiler feed water 288. Synthesis gas leaving the feedwater heater 258 is preferably around 160° C. It is cooled down to 40° C. using a fin-fan cooler 261 and a synthesis gas cooler 264 fed by cooling water 266. The cooled synthesis gas 248 then enters a knock-out drum 268 where water is removed from the bottoms as process condensate stream 270 which, although not shown, can be recycled for use as feedwater, and the cooled synthesis gas 272 is recovered overhead.

The cooled synthesis gas stream 272 is optionally compressed in a synthesis gas compressor 274 to produce a synthesis gas product 276. Depending on the operating pressure of the oxygen transport membrane based reforming system, pressure of the recovered synthesis gas is preferably in the range of about 10 bar and 35 bar and more preferably in the range of 12 bar and 30 bar. The module of the synthesis gas produced in the described embodiment is typically less than about 2.0 and often less than about 1.9, whereas for some synthesis gas applications such as methanol synthesis, the desired module of the synthesis gas is preferably in the range of about 2.0 to 2.2. Use of an adiabatic pre-reformer upfront of the OTM reactor can increase the module by about 0.05 to 0.1 relative to the configuration without a pre-reformer. With a heated pre-reformer, it becomes possible to achieve higher modules, preferably greater than 2 and definitely greater than 1.9. The exact module value depends on the operating temperature.

The oxygen transport membrane elements or tubes used in the embodiments disclosed herein preferably comprise a composite structure that incorporates a dense layer, a porous support and an intermediate porous layer located between the dense layer and the porous support. Each of the dense layer and the intermediate porous layer are capable of conducting oxygen ions and electrons at elevated operational temperatures to separate the oxygen from the incoming air stream. The porous support layer would thus form the permeate side. The dense layer and the intermediate porous layer preferably comprise a mixture of an ionic conductive material and an electrically conductive material to conduct oxygen ions and electrons, respectively. The intermediate porous layer preferably has a lower permeability and a smaller average pore size than the porous support layer to distribute the oxygen separated by the dense layer towards the porous support layer.

In the preferred embodiments, the oxygen transport membrane tubes include a mixed phase oxygen ion conducting dense ceramic separation layer comprising a mixture of a zirconia based oxygen ion conducting phase and a predominantly electronic conducting perovskite phase. This thin, dense separation layer is implemented on a thicker inert, porous support. The intermediate porous layer can have a thickness of between about 10 microns and about 40 microns, a porosity of between about 25 percent and about 40 percent and an average pore diameter of between about 0.5 microns and about 3 microns. The dense layer can have a thickness of between about 10 microns and about 30 microns. The porous surface exchange layer can be provided with a thickness of between about 10 microns and about 40 microns, a porosity of between about 30 percent and about 60 percent and a pore diameter of between about 1 microns and about 4 microns and the support layer can have a thickness of between about 0.5 mm and about 10.0 mm, but preferably 0.9 mm and a pore size no greater than 50 microns. The intermediate porous layer can contain a ceramic mixture of about 60 percent by weight of $(La_{0.825}Sr_{0.175})_{0.96}Cr_{0.76}Fe_{0.225}V_{0.015}O_{3-\delta}$, remainder 10Sc1YSZ, whereas the dense layer can be formed of a ceramic mixture of about 40 percent by weight of $(La_{0.825}Sr_{0.175})_{0.94}Cr_{0.72}Mn_{0.26}V_{0.02}O_{3-x}$, remainder 10Sc1YSZ and the porous surface exchange layer can be formed by a ceramic mixture of about 50 percent by weight of $(La_{0.8}Sr_{0.2})_{0.98}MnO_{3-\delta}$, remainder 10Sc1CeSZ.

Oxidation catalyst particles or a solution containing precursors of the oxidation catalyst particles are optionally located in the intermediate porous layer and in the thicker inert, porous support adjacent to the intermediate porous layer. The oxidation catalyst particles contain an oxidation catalyst selected to promote oxidation of the partially reformed synthesis gas stream in the presence of the permeated oxygen when introduced into the pores of the porous support, on a side thereof opposite to the intermediate porous layer. The oxidation catalyst can be gadolinium doped ceria. Further, a porous surface exchange layer can be provided in contact with the dense layer opposite to the intermediate porous layer. In such case, the porous surface exchange layer would form the retentate side. The support layer is preferably formed from a fluorite structured material, for example 3 mol % yttria stabilized zirconia, or 3YSZ.

Figure 4:
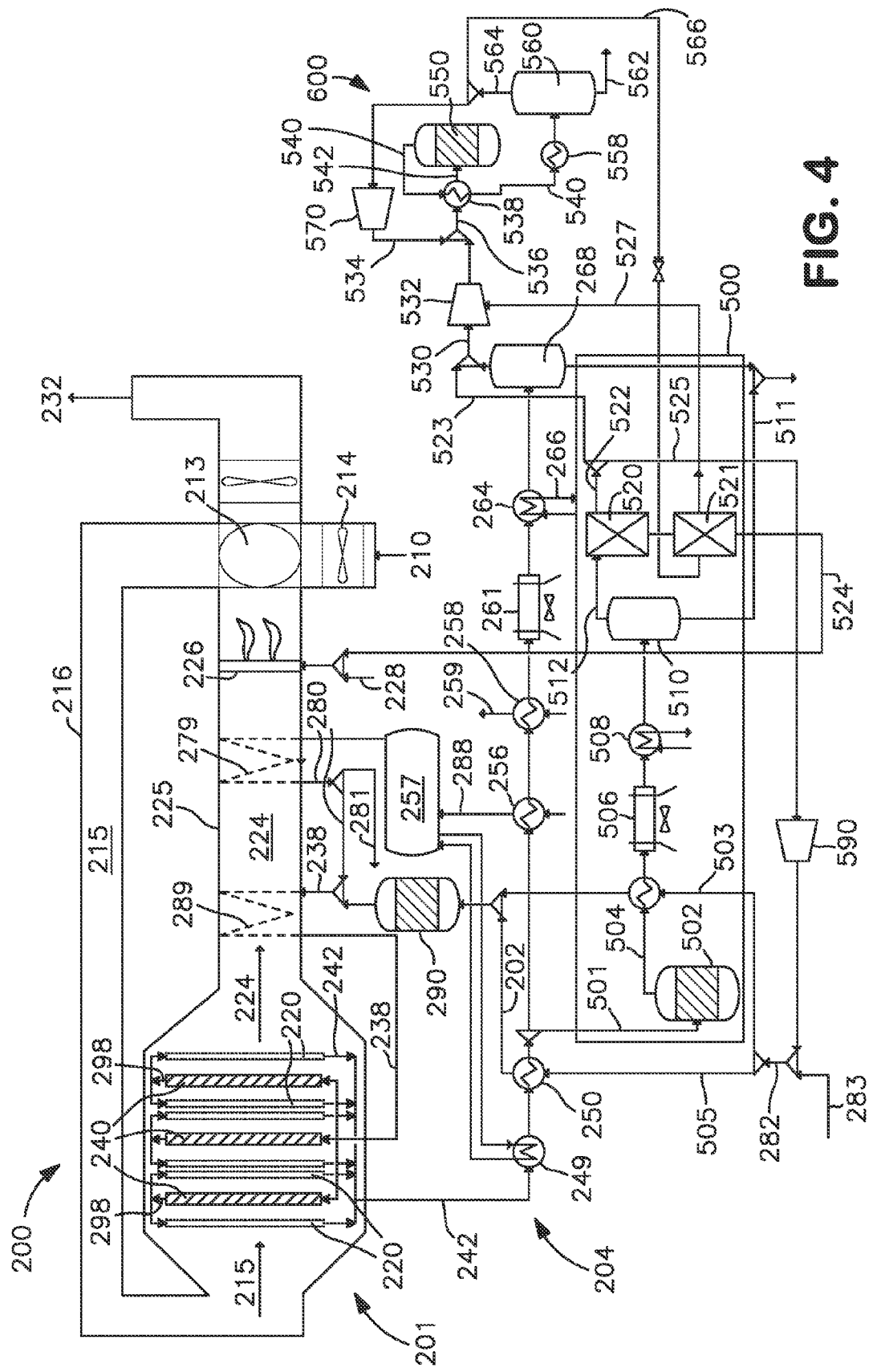
FIG. 4 is a schematic illustration of another embodiment of an oxygen transport membrane based reforming system configured to carry out primary reforming process, secondary reforming process, and synthesis gas conditioning for use in an integrated with a methanol production system.

Turning now to FIG. 4, there is shown a schematic illustration of one embodiment of a methanol production scheme using an oxygen transport membrane based reforming system and system that is configured to carry out a primary reforming process, a secondary reforming process, and a synthesis gas conditioning process. In many regards, this embodiment is similar to the embodiment of FIG. 3 and, for sake of brevity, the description of the common aspects of the two embodiments will not be repeated here, rather, the following discussion shall focus on the differences between embodiments in FIG. 3 and FIG. 4.

The notable difference between the embodiments shown in FIG. 4 compared to the embodiment shown in FIG. 3 is the inclusion of a synthesis gas module management section 500. In the illustrated embodiment, up to about 20% and more preferably up to about 15% of the directly cooled synthesis gas 501 is diverted to the synthesis gas module management section 500, and more particularly to a shift reactor 502 to generate additional hydrogen and carbon dioxide via the Water Gas Shift reaction:

$$CO + H_2O \rightarrow CO_2 + H_2$$

Since the Water Gas Shift reaction is exothermic, the shifted synthesis gas 504 leaves the shift reactor 502 at a temperature greater than the directly cooled synthesis gas, and preferably at a temperature of around 435° C. A portion of the sensible energy in this stream is recovered by heating a portion of the natural gas and hydrogen feed stream 503, preferably between about 20% and 45% of the hydrocarbon feed stream. The remaining portion of the natural gas and hydrogen feed stream 505 is directed to the fuel pre-heater 250, as described with reference to FIG. 3. The diverted portion of the natural gas and hydrogen feed stream 503 and the remaining portion of the natural gas and hydrogen feed stream 505 are recombined upstream of the sulfur removal device 290.

The shifted synthesis gas 504 is subsequently cooled with a fin-fan cooler 506 and synthesis gas cooler 508 to about 38° C. A knockout drum 510 is used to remove moisture as a condensate stream 511 before the cooled shifted synthesis gas 512 is directed as an influent stream to a hydrogen pressure swing adsorption unit 520 which produces a hydrogen gas effluent 522 and a tail gas or off-gas effluent 524. A portion of the hydrogen gas effluent 523, preferably about 50% to 75% by volume, is recovered and mixed with the synthesis gas stream 272, as shown in FIG. 4. The remaining portion of the hydrogen gas effluent 525 is optionally compressed using a hydrogen compressor 590 to a pressure of between about 10 bar and 30 bar, is directed to and mixed with the natural gas feed 283 prior to desulfurization to produce the natural gas and hydrogen feed stream 282. It is important to note that the hydrogen compressor 590 may not be required in this embodiment if the recycled hydrogen originates from the hydrogen separation unit 521 since it is only fed by the high pressure methanol purge 566.

By combining a portion 523 of the hydrogen gas 522 produced in the synthesis gas module management section 500 with the cooled synthesis gas stream 272, the module of the combined stream 530 is adjusted to be in the desired range of about 2.0 to 2.2. The precise module is controlled by suitably adjusting the amount of directly cooled synthesis gas being diverted to the shift reactor 502 and the amount of hydrogen gas combined back with the cooled synthesis gas stream 272. The tail gas or off-gas effluent 524 from the hydrogen pressure swing adsorption unit 520, typically has a higher heating value of about 240 BTU/scf, and is available for use as fuel for the duct burner 226 in the oxygen transport membrane based reforming system 201. Use of the tail gas or off-gas 524 as a fuel for the duct burner 226 in the oxygen transport membrane based reforming system 201 reduces the overall consumption of natural gas by the system 200.

The combined stream 530 having an adjusted module between about 2.0 and 2.2 is then compressed to a pressure between 1100 psia and 1500 psia in compressor 532 and mixed with a methanol recycle stream 534. This mixed stream 536 of compressed synthesis gas and methanol recycle is indirectly heated in heat exchanger 538 by the synthesized methanol stream 540 to a temperature between about 175° C. and 300° C. The heated stream 542 is directed to the methanol synthesis reactor 550. In this methanol synthesis reactor 550, hydrogen, carbon monoxide and carbon dioxide are consumed to produce methanol and water in an exothermic process through the following reactions:

$$CO + 2H_2 \rightarrow CH_3OH$$

$$CO_2 + 3H_2 \rightarrow CH_3OH + H_2O$$

The heat generated in the methanol synthesis reaction is used for steam production and/or for preheating of the synthesis gas feed. Temperature at the outlet of the methanol reactor is typically between about 200° C. and about 260° C. This methanol synthesis stream 540 is cooled down to about 38° C. in heat exchanger 538 and cooler 558 before entering a separator 560 where the crude methanol stream 562 containing mostly methanol, water and trace amounts of other species (e.g. dimethyl ether, ethanol and higher alcohols), is separated in the bottoms and sent to further distillation steps for final purification. Most of the overhead stream 564 from the separator 560 is recycled back to the methanol synthesis reactor 550 via recycle compressor 570 to increase the carbon conversion to methanol. The recycle compressor 570 is required to compensate for pressure drop across the methanol synthesis reactor 550 and associated equipment, e.g. heat exchangers and coolers.

A small portion of the overhead stream 564, typically between about 1% and 4% is purged from the methanol synthesis loop 600 to prevent buildup of inerts in the methanol synthesis loop 600. The typical composition of the purge stream 566 is as follows: 75% hydrogen, 3% carbon dioxide, 12% carbon dioxide, 3% nitrogen, and 7% methane, with a higher heating value of about 325 BTU/scf. The methanol loop purge stream 566 is fed as a supplemental influent stream to another hydrogen separation device 521, such as another hydrogen pressure swing adsorption unit or hydrogen separation membrane to supplement the hydrogen recovery. The hydrogen separation device 521 generates a higher pressure hydrogen stream 527, which can be directly fed to an intermediate stage of compressor 532. Although not shown, a portion of the methanol loop purge stream 566 may also be recirculated to the oxygen transport membrane based reforming system.

It should be noted that the illustrated embodiment improves the synthesis gas module to make it amenable for methanol synthesis. However, the arrangement requires additional capital expense by adding a shift reactor, knockout drum, hydrogen pressure swing adsorption units, hydrogen compressor and several heat exchangers.

Figure 5:
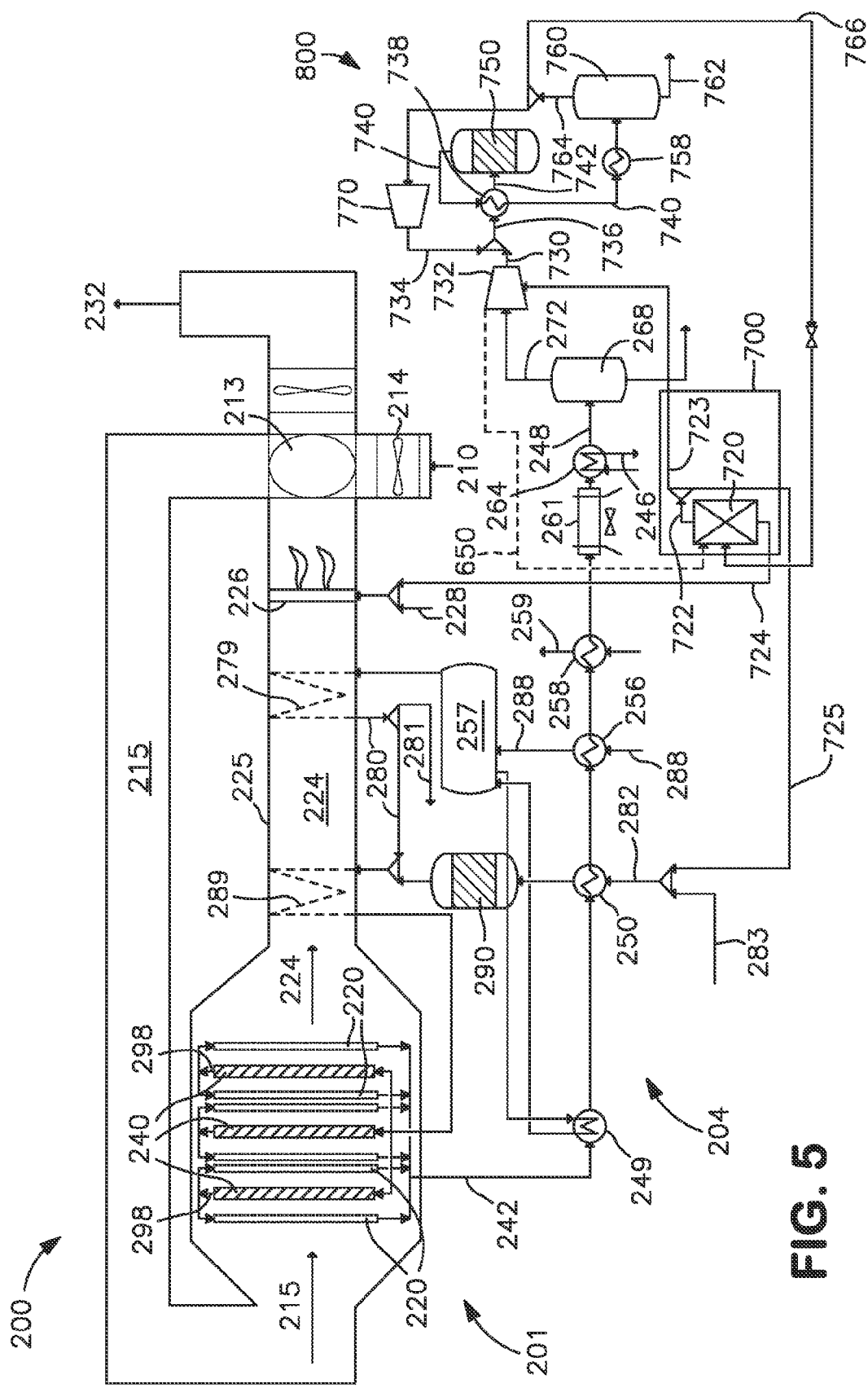
FIG. 5 is a schematic illustration of another embodiment of an oxygen transport membrane based reforming system configured to carry out primary reforming process, secondary reforming process, and synthesis gas conditioning for use in an integrated with a methanol production system.

FIG. 5 shows yet another embodiment of a methanol production scheme using an oxygen transport membrane based reforming system and assembly that is also configured to carry out a primary reforming process, a secondary reforming process, and a synthesis gas conditioning process. In many regards, this embodiment of FIG. 5 is also similar to the embodiment of FIG. 3 and, for sake of brevity, the description of the common aspects of the two embodiments will not be repeated here, rather, the following discussion shall focus on the differences between embodiments in FIG. 3 and FIG. 5.

The notable difference between the embodiments shown in FIG. 5 compared to the embodiment shown in FIG. 3 is the inclusion of an alternate synthesis gas module management section 700. In the illustrated embodiment, the synthesis gas module management section 700 comprises a high pressure hydrogen pressure swing adsorption unit 720. The methanol purge stream 766, which is typically at a pressure between 70 bar and 100 bar depending on the operating pressure of the methanol synthesis reactor 750, is directed as an influent stream to the hydrogen pressure swing adsorption unit 720 which produces a hydrogen gas effluent 722 and a tail gas or off-gas effluent 724. While the hydrogen pressure swing adsorption unit 720 can be designed to operate at the pressure of the methanol purge stream, it is desirable to design the hydrogen pressure swing adsorption unit 720 to operate at a pressure in the range of 40-55 bar to match the pressure at the exit of the first stage of compression in the synthesis gas compressor 732. A portion of the hydrogen gas effluent 723, preferably about 85% to 95% by volume, is recovered and eventually mixed in the compressor 732 with the cooled synthesis gas stream 272, as shown in FIG. 5.

The remaining portion of the hydrogen gas effluent 725, preferably between about 5% and 15% by volume is directed to and mixed with the natural gas feed 283 prior to desulfurization to produce the natural gas and hydrogen feed stream 282. However, unlike the embodiment of FIG. 4, a hydrogen compressor may not be required in this embodiment if the hydrogen pressure swing adsorption unit 720 is configured to operate at between about 40 bar and 55 bar since it is only fed by the high pressure methanol purge stream 766. Tail gas or off-gas effluent 724 from the hydrogen pressure swing adsorption unit 720 is used as a portion of the fuel in the duct burner 226 with natural gas 228.

By combining a portion of the hydrogen gas 723 produced in the synthesis gas module management section 700 with the cooled synthesis gas stream 272, the module of the combined stream 730 is adjusted to be in the desired range of about 2.0 to 2.2. The precise module is controlled by suitably adjusting the amount of hydrogen gas combined back with the cooled synthesis gas stream 272. Similar to the embodiment of FIG. 4, the tail gas or off-gas effluent 724 from the hydrogen pressure swing adsorption unit 720 is available for use as fuel for the duct burner 226 in the oxygen transport membrane based reforming system 201 which reduces the overall consumption of natural gas by the system. The tail gas or off-gas 524 has a heating value of about 240 BTU/scf.

The cooled synthesis gas stream 272 and portion of the hydrogen stream 723 are combined and compressed to a pressure between 1100 psia and 1500 psia in compressor 732 and mixed with a methanol recycle stream 734 described hereinafter. This mixed stream 736 of compressed synthesis gas and methanol recycle is indirectly heated in heat exchanger 738 by the synthesized methanol stream 740 to a temperature between about 175° C. and 300° C. The heated stream 742 is directed to the methanol synthesis reactor 750. In this methanol synthesis reactor 750, hydrogen, carbon monoxide and carbon dioxide are consumed to produce methanol and water.

As above, the heat generated in the exothermic methanol synthesis reaction is preferably used for steam production and/or for preheating of the synthesis gas feed to the methanol synthesis reactor. Temperature at the outlet of the methanol reactor is typically between about 200° C. and about 260° C. This methanol synthesis stream 740 is cooled down to about 38° C. in heat exchanger 738 and cooler 758 before entering a separator 760 where the crude methanol stream 762 containing mostly methanol, water and trace amounts of other species (e.g. dimethyl ether, ethanol and higher alcohols), is separated in the bottoms and sent to further distillation steps for final purification. Most of the overhead stream 764 from the separator 760 is recycled back to the methanol synthesis reactor 750 via recycle compressor 770 to increase the carbon conversion to methanol. The recycle compressor 770 is required to compensate for pressure drop across the methanol synthesis reactor 750 and associated equipment, e.g. heat exchangers and coolers.

A portion of the overhead stream 764, typically between about 4% and 10% is purged from the methanol synthesis loop 800 to prevent buildup of inerts in. The typical composition of purge stream 766 in the embodiment of FIG. 5 is as follows: 75% hydrogen, 4% carbon dioxide, 15% carbon dioxide, 2% nitrogen, and 4% methane, with a heating value of about 300 BTU/scf. As indicated above, the methanol loop purge stream 766 is fed as the primary influent stream to the hydrogen pressure swing adsorption unit 720 as shown in FIG. 5.

During start-up of the system, a portion of the partially compressed synthesis gas 650 is fed as an influent stream preferably from an intermediate stage of synthesis gas compressor 732 to the hydrogen pressure swing adsorption unit to achieve the desired synthesis gas module until the methanol loop 800 is operational and requirements can be met completely by the purge stream 766 from the methanol loop 800.

It should be noted that the embodiment of FIG. 5, like that of FIG. 4 produces the same amount of methanol and improves the synthesis gas module, but unlike the embodiment of FIG. 4 the arrangement of FIG. 5 requires less capital expense as a shift reactor, knockout drum, and several heat exchangers are not required and the complexity of the hydrogen separation system is reduced. For example, one embodiment of FIG. 4 contains a high pressure hydrogen separation unit 521 (e.g. high pressure hydrogen pressure swing adsorption unit) and a low pressure hydrogen pressure swing adsorption unit 520. By contrast, the corresponding embodiment of FIG. 5 would include one hydrogen pressure swing adsorption unit 720.

Possible modifications to the embodiments presented in FIGS. 4 and 5 include the use of a turbo expander to recover power when letting down the pressure from the methanol purge from a high pressure of about 90 bar in the methanol loop to a lower pressure of about 20 bar for the oxygen transport membrane based reformers or the hydrogen pressure swing adsorption unit. Another possible modification involves the use of a hydrogen separation membrane to separate hydrogen from the methanol purge streams in lieu of separation in the hydrogen pressure swing adsorption unit.

Further modifications to the embodiments presented in FIGS. 3-5 include the use of a natural gas fired heater in lieu of or in addition to the indirect heat exchange with coils disposed in the retentate duct of the oxygen transport membrane based reforming system to heat one or more of the following streams: the natural gas and hydrogen feed stream; the mixed feed stream; and incoming air stream and/or to generate superheated steam from saturated steam. In this case, some of the tail gas or off-gas effluent from the hydrogen separation system in the module management section can be used as fuel in the fired heater. The use of the natural gas fired heater is particularly advantageous to facilitate start-up of the oxygen transport membrane based reforming system and assembly.

While the present inventions have been characterized in various ways and described in relation to preferred embodiments, as will occur to those skilled in the art, numerous, additions, changes and modifications thereto can be made without departing from the spirit and scope of the present inventions as set forth in the appended claims.

What is claimed is:

1. A method for producing methanol using an oxygen transport membrane based reforming system, wherein said system comprises at least one reforming reactor and at least one oxygen transport membrane reactor in close proximity to said at least one reforming reactor, the method comprising the steps of:
separating oxygen from an oxygen containing stream with one or more catalyst containing oxygen transport membrane reactors to produce an oxygen permeate and an oxygen depleted retentate stream, the catalyst being contained within tubes on the permeate side of the oxygen transport membrane reactors;
partially reforming a combined feed stream comprising natural gas and steam in a reforming reactor in the presence of a reforming catalyst and radiant heat transferred from the oxygen transport membrane reactor to produce a partially reformed synthesis gas stream;
directing the partially reformed synthesis gas stream to the permeate side of the one or more catalyst containing oxygen transport membrane reactor;
reacting a portion of the partially reformed synthesis gas stream contacting the permeate side of the catalyst containing oxygen transport membrane reactor with the oxygen permeate to generate a heated reaction product stream comprising oxidation products and heat, and wherein a portion of the heat is transferred by radiation to the reforming reactor, a portion of the heat is used within the oxygen transport membrane reactor and a portion of the heat is transferred by convection to the oxygen-depleted retentate stream;
reforming the partially reformed synthesis gas stream in the catalyst containing oxygen transport membrane reactor in the presence of the heat generated as a result of the oxidation reaction to produce a final reformed synthesis gas product stream;
directing the final reformed synthesis gas product stream to a methanol synthesis and purification system;
synthesizing the final reformed synthesis gas product stream into crude methanol; and
purifying the crude methanol to a finished methanol product.

2. The method of claim 1 further comprising the steps of recovering unconverted hydrogen and methane slip during the methanol synthesis step; and recycling a portion of the unconverted hydrogen and methane slip recovered during the methanol synthesis and purification steps to the oxygen transport membrane based reforming system.

3. The method of claim 1 wherein the oxygen transport membrane tubes comprise:
multilayered dual phase ceramic tubes having a dense layer, a porous support and an intermediate porous layer capable of conducting oxygen ions at an elevated operational temperature; and a combustion catalyst disposed in or proximate to the porous support layer and proximate to the permeate side of the oxygen transport membrane tubes to facilitate reaction of a portion of the partially reformed synthesis gas stream contacting the permeate side of the oxygen transport membrane tubes with the permeated oxygen stream.

4. The method of claim 1 further comprising the step of reheating the oxygen-depleted retentate stream to a temperature of from about 1000° C. to about 1200° C. using a duct burner disposed within or proximate to the oxygen transport membrane based reforming system wherein the duct burner is configured to react a supplemental fuel stream and residual oxygen in the oxygen depleted retentate stream.

5. The method of claim 1 further comprising the step of directly cooling the final reformed synthesis gas stream to a temperature of about 400° C. or less.

6. The method of claim 5 further comprising the steps of:
diverting a portion of the cooled synthesis gas stream to a module management system to produce hydrogen gas via a water gas shift reaction and hydrogen separation; and
combining a portion of the produced hydrogen gas with the remaining portion of the synthesis gas stream to produce a combined synthesis gas product stream having a module between about 2.0 to 2.2.

7. The method of claim 6 further comprising the steps of recovering unconverted hydrogen and methane slip during the methanol synthesis and/or purification steps; and recycling a portion of the unconverted hydrogen and methane slip recovered during the methanol synthesis step to the module management system.

8. The method of claim 7 further comprising the step of directing a portion of the unconverted hydrogen to the combined feed stream.

9. The method of claim 7 further comprising the steps of:
reheating the oxygen-depleted retentate stream to a temperature of between about 1000° C. and 1200° C. using a duct burner disposed within or proximate to the oxygen transport membrane based reforming system, wherein the duct burner is configured to combust a supplemental fuel stream and residual oxygen in the oxygen depleted retentate stream to heat the incoming oxygen containing stream via indirect heat exchange in a ceramic regenerator; and
directing a portion of an off-gas generated by the module management system to the duct burner to form a portion of the supplemental fuel stream.

10. The method of claim 6 wherein the step of diverting a portion of the cooled synthesis gas stream to a module management system to produce hydrogen gas further comprises:
diverting a portion of the cooled synthesis gas stream to a shift reactor;
cooling the shifted synthesis gas;
removing moisture from the cooled shifted gas stream; and
directing the cooled shifted gas stream to a hydrogen pressure swing adsorption unit to produce the hydrogen gas and an off-gas.

11. The method of claim 6 wherein the diverted portion of the synthesis gas stream is less than about 20 percent by volume of the cooled synthesis gas stream.

12. The method of claim 1 further comprising the steps of:
recovering unconverted hydrogen and methane slip during the methanol synthesis and/or purification steps;
recycling a portion of the unconverted hydrogen and methane slip recovered during the methanol synthesis and/or purification steps to a hydrogen pressure swing adsorption system to produce hydrogen;
combining a portion of the produced hydrogen with the synthesis gas stream to produce a combined synthesis gas product stream having a module between about 2.0 to 2.2; and directing a portion of the hydrogen produced by the hydrogen pressure swing adsorption system to the combined feed stream.

13. The method of claim 12 further comprising the steps of:
reheating the oxygen-depleted retentate stream to a temperature of between about 1000° C. and 1200° C. using a duct burner disposed within or proximate to the oxygen transport membrane based reforming system wherein the duct burner is configured to combust a supplemental fuel stream and residual oxygen in the oxygen depleted retentate stream to heat the incoming oxygen containing stream via indirect heat exchange in a ceramic regenerator; and directing a portion of an off-gas generated by the module management system to the duct burner to form a portion of the supplemental fuel stream.

14. A method of adjusting module of synthesis gas in methanol plant, wherein said synthesis gas is produced in an oxygen transport membrane based reforming system comprising at least one reforming reactor and at least one oxygen transport membrane reactor in close proximity to said at least one reforming reactor, the method comprising the steps of:
reforming a combined feed stream of natural gas and steam partially in a reforming reactor in the presence of reforming catalyst and radiant heat transferred from the oxygen transport membrane reactor and then subsequently reforming said combined feed stream in the presence of an oxygen containing permeate, one or more catalysts and heat in an oxygen transport membrane reactor within the oxygen transport membrane based reforming system to produce a synthesis gas stream and an oxygen depleted retentate stream;
diverting a portion of the synthesis gas stream to a module management system to generate hydrogen gas via a water gas shift reaction and hydrogen separation;
combining a portion of the generated hydrogen with the remaining portion of the synthesis gas stream to produce a combined synthesis gas product stream having a module between about 2.0 to 2.2;
directing the combined synthesis gas product stream to a methanol synthesis system;
recovering unconverted hydrogen and methane slip from the methanol synthesis system; and
recycling a portion of the unconverted hydrogen and methane slip recovered during the methanol synthesis to the module management system.

15. The method of claim 14 further comprising the step of directing a portion of the hydrogen generated by the module management system to the hydrocarbon feed stream of the oxygen transport membrane based reforming system.

16. The method of claim 14 further comprising the steps of:
reheating the oxygen-depleted retentate stream to a temperature of between about 1900° F. and 2200° F. using a duct burner disposed within or proximate to the oxygen transport membrane based reforming system wherein the duct burner is configured to combust a supplemental fuel stream and residual oxygen in the oxygen depleted retentate stream to heat an incoming air stream via indirect heat exchange in a ceramic regenerator; and directing a portion of an off-gas generated by the module management system to the duct burner to form a portion of the supplemental fuel stream.

17. A method of adjusting the module of a synthesis gas stream for use in a methanol plant wherein said synthesis gas is produced in an oxygen transport membrane based reforming system comprising at least one reforming reactor and at least one oxygen transport membrane reactor in close proximity to said at least one reforming reactor, the method comprising the steps of:
reforming a combined feed stream of natural gas and steam partially in a reforming reactor in the presence of reforming catalyst and radiant heat transferred from the oxygen transport membrane reactor and then subsequently reforming said combined feed stream in the presence of an oxygen containing permeate separated from an oxygen containing feed stream, one or more catalysts and heat in an oxygen transport membrane reactor within the oxygen transport membrane based reforming system to produce a synthesis gas stream and an oxygen depleted retentate stream;
directing the synthesis gas stream to a methanol synthesis and purification system;
recovering unconverted hydrogen and methane slip from the methanol synthesis and methanol purification system;
recycling a portion of the unconverted hydrogen and methane slip recovered during the methanol synthesis and methanol purification to a hydrogen pressure swing adsorption system to generate hydrogen;
combining a portion of the generated hydrogen with the synthesis gas stream to produce a combined synthesis gas product stream having a module between about 2.0 to 2.2; and
directing a portion of the hydrogen generated by the hydrogen pressure swing adsorption system to the hydrocarbon feed stream.

18. The method of claim 17 further comprising the steps of: reheating the oxygen-depleted retentate stream to a temperature of between about 1000° C. and 1200° C. using a duct burner disposed within or proximate to the oxygen transport membrane based reforming system wherein the duct burner is configured to combust a supplemental fuel stream and residual oxygen in the oxygen depleted retentate stream to heat the oxygen containing feed stream via indirect heat exchange in a ceramic heat exchanger.

19. The method of claim 17 further comprising the step of diverting a portion of the synthesis gas stream to the hydrogen pressure swing adsorption system to generate hydrogen gas.

20. The method of claim 12 further comprising the step of directly cooling the final reformed synthesis gas stream to a temperature of about 400° C. or less.

21. The method of claim 20 further comprising the step of diverting a portion of the cooled synthesis gas stream to the hydrogen pressure swing adsorption system.

\* \* \* \* \*